United States Patent
Guieze (10) Patent No.: US 8,621,912 B2
(45) Date of Patent: Jan. 7, 2014

(54) NATURAL GAS ANALYZER ON A MICRO-CHIP

(75) Inventor: Paul Guieze, Fontenailles (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 365 days.

(21) Appl. No.: 12/745,575

(22) PCT Filed: Nov. 17, 2008

(86) PCT No.: PCT/EP2008/009700
§ 371 (c)(1),
(2), (4) Date: Sep. 14, 2010

(87) PCT Pub. No.: WO2009/068201
PCT Pub. Date: Jun. 4, 2009

(65) Prior Publication Data
US 2011/0011156 A1    Jan. 20, 2011

(30) Foreign Application Priority Data

Nov. 30, 2007  (EP) .................................... 07291432

(51) Int. Cl.
*G01N 30/04*   (2006.01)
*G01N 30/02*   (2006.01)
*B01D 53/14*   (2006.01)

(52) U.S. Cl.
USPC ............................ 73/23.42; 73/23.38; 96/104

(58) Field of Classification Search
USPC ................... 73/23.35, 23.38, 123.42; 96/104
See application file for complete search history.

(56) References Cited

U.S. PATENT DOCUMENTS

| | | | |
|---|---|---|---|
| 3,030,798 A | | 4/1962 | Lichtenfels |
| 3,087,112 A | | 4/1963 | Pfefferle |
| 3,422,665 A | * | 1/1969 | Haase ................................ 95/86 |
| 3,607,075 A | | 9/1971 | Wolf et al. |
| 4,467,038 A | | 8/1984 | Scott |
| 4,935,040 A | * | 6/1990 | Goedert ........................ 73/23.22 |
| 5,132,012 A | | 7/1992 | Miura et al. |
| 5,637,135 A | * | 6/1997 | Ottenstein et al. ............... 96/101 |
| 5,997,708 A | * | 12/1999 | Craig ............................ 204/601 |
| 6,258,263 B1 | | 7/2001 | Henderson et al. |

(Continued)

FOREIGN PATENT DOCUMENTS

| | | |
|---|---|---|
| GB | 1446940 | 8/1976 |
| WO | 2005/114169 | 12/2005 |

OTHER PUBLICATIONS

Journal of Chromatography A, 775 [1997] Etiope G, "Evaluation of a micro gas chromatographic technique for environmental analyses of CO2 and c1-c6 Alkanes", pp. 243-249.

*Primary Examiner* — Hezron E Williams
*Assistant Examiner* — Nathaniel Kolb
(74) *Attorney, Agent, or Firm* — Cameron R. Sneddon (57) ABSTRACT

A miniaturized gas analyzer formed onto a micro-chip and a method of separating components from a composite gas using the miniaturized gas analyzer are disclosed. The gas analyzer includes an injector block and two column blocks arranged in series along an analytical path. The injector block receives the composite gas and a carrier gas to create a gas sample. The gas sample is then injected into the column blocks to separate the components of the composite gas. Further, a valve used within the miniaturized gas analyzer is disclosed, in which the valve is formed onto the micro-chip and includes a flexible membrane and a rigid substrate.

14 Claims, 9 Drawing Sheets

(56) References Cited

U.S. PATENT DOCUMENTS

| | | | |
|---|---|---|---|
| 6,386,014 B1* | 5/2002 | Butch | 73/23.35 |
| 6,772,513 B1 | 8/2004 | Frye-Mason et al. | |
| 2004/0043479 A1 | 3/2004 | Briscoe et al. | |
| 2005/0142662 A1* | 6/2005 | Bonne | 436/149 |
| 2006/0196247 A1* | 9/2006 | Gamache et al. | 73/23.42 |
| 2006/0210441 A1 | 9/2006 | Schmidt et al. | |
| 2007/0166199 A1* | 7/2007 | Zhou et al. | 422/100 |

\* cited by examiner

NATURAL GAS ANALYZER ON A MICRO-CHIP

CROSS-REFERENCE TO RELATED APPLICATIONS

The present application is based on and claims priority to EP Application No. 07291432.8, filed 30 Nov. 2007; and International Patent Application No. PCT/EP2008/009700, filed 17 Nov. 2008. The entire contents of each are herein incorporated by reference.

BACKGROUND

1. Field of the Disclosure

The invention generally relates to miniaturized natural gas analyzers that use gas chromatography. Specifically, it relates to a natural gas analyzer that is machined onto a single micro-chip and uses gas chromatography for analyzing natural gas.

2. Background Art

Gas chromatography (GC) has been used for more than 50 years within the field of natural gas analysis to separate and quantify the different components found within natural gas. Over this time period, the technology used within gas chromatographs has generally remained the same since when the technology was originally introduced into the natural gas industry. For example, the equipment used for gas chromatographs within laboratories has remained fairly large and cumbersome, thereby limiting the adaptability and versatility for the equipment. These limitations may be a strain on resources, as moving the equipment around may be a challenge that requires an unnecessary amount of time and assets. Because of the bulkiness of the existing GC analyzers for gas analysis this analysis is typically performed off-line in a laboratory environment.

Within about the past 10 years, certain efforts have been made in reducing the size of GC gas analyzers mainly in applications other than natural gas.

An example of a miniaturized gas chromatograph is disclosed in U.S Published patent application No. 2006/0210441 A1 to Schmidt ("Schmidt"). This gas describes a GC gas analyzer that includes an injector, a separation column, and a detector all combined onto a circuit board (such as a printed circuit board). The injector then incorporates a type of slide valve, which is used to introduce a defined volume of liquid or gas. Schmidt asserts that by using this slide valve, the gas chromatograph may create a reliable and reproducible gas sample. This gas sample is then injected into the column to separate the gas sample into various components.

Though Schmidt describes a smaller gas chromatograph for manufacturing, the chromatographs are still slow to develop for use within the natural gas industry. For example, there are some gas chromatographs that are manufactured commercially for use within the natural gas industry, but these chromatographs are designed specifically for analyzing domestic natural gas. Within the spectrum of natural gas, domestic natural gas consists of only a small portion of the spectrum. As such, this suggests that these domestic gas chromatographs are designed to analyze only a small portion of the natural gas spectrum, therefore not being useful or applicable outside of this small application. For example, natural gases that are found within hydrocarbon fields may vary from having only a trace of carbon dioxide to having over 90% carbon dioxide. This large variation within the ranges of the components of natural gas makes it difficult for gas chromatographs to correctly separate and analyze the components within the natural gas. As such, current models and techniques used within gas chromatographs in the natural gas industry may be improved to have smaller and more versatile gas analyzers.

SUMMARY OF INVENTION

In one aspect, the embodiments disclosed herein relate to a miniaturized gas analyzer formed onto a micro-chip. The gas analyzer includes an injector block and first and second column blocks. The injector block includes a first input to receive composite gas, a second input to receive carrier-gas, and an output to expel the received composite gas carried by the carrier-gas as a gas sample. Each of the first and second column blocks include a separation column and a detector. The separation column has an input to receive the gas sample and is used to separate the gas sample into components. The detector is then arranged to receive the components of the gas sample from an output of the separation column and to differentiate the components into resolved components and unresolved components. Further, the injector block and the first and second column blocks are arranged in series on an analytical path of the micro-chip such that the gas sample expelled by the output of the injector block is received within the first column block. The unresolved component is then expelled by the first column block and received within the second column block.

In another aspect, the embodiments disclosed herein relate to a method of analyzing natural gas using a miniaturized gas analyzer formed onto a micro-chip. The method includes sampling a volume of natural gas with a sampling loop of an injector block to create a gas sample. The gas sample is then injected from the injector block to a first column block using carrier-gas from a reference path. Further, the gas sample is separated into an unresolved component and a resolved component using a separation column of the first column block.

Other aspects and advantages of the embodiments disclosed herein will be apparent from the following description and the appended claims.

DETAILED DESCRIPTION

Specific embodiments of the present invention will now be described in detail with reference to the accompanying figures. Like elements in the various figures may be denoted by like reference numerals for consistency.

In the following detailed description of embodiments of the present disclosure, numerous specific details are set forth in order to provide a more thorough understanding of the invention. However, it will be apparent to one of ordinary skill in the art that the present invention may be practiced without these specific details. In other instances, well-known features have not been described in detail to avoid unnecessarily complicating the description.

As used herein, the embodiments disclosed herein are described for separating components from a gas sample of natural gas. However, those having ordinary skill in the art will appreciate that any composite gas known in the art, and not only natural gas, may be used to be separated into smaller components of the gas in accordance with embodiments disclosed herein Embodiments disclosed herein relate to a gas analyzer that is disposed or formed upon a micro-chip. The gas analyzer is connected to a natural gas source and a carrier-gas source, and includes an injector block and a plurality of column blocks. The injector block of the gas analyzer is used to create a gas sample from the natural gas, and then uses the carrier-gas to carry the gas sample through the remainder of the gas analyzer (i.e., the column blocks). As the sample gas is received within each of the column blocks, the gas sample is separated into at least two components. These components may then be eluted from the gas analyzer, or the components may be passed onto other column blocks for further separation.

Additionally, because this gas analyzer is disposed upon a micro-chip, embodiments disclosed herein relate to a valve, such as a micro-valve, that may be incorporated into the gas analyzer. The valve includes the micro-chip, a flexible membrane, and a rigid substrate. A loop groove and a conduit are machined or formed onto the micro-chip, in which the flexible membrane is disposed on top of the micro-chip and the rigid membrane is disposed on top of the flexible membrane. The conduit is formed in a way such that pressure may be used to push the flexible membrane to open and close the conduit. As the conduit then open and closes, gas flowing through the conduit may pass through or be impeded, thereby opening and closing the valve.

Figure 1:
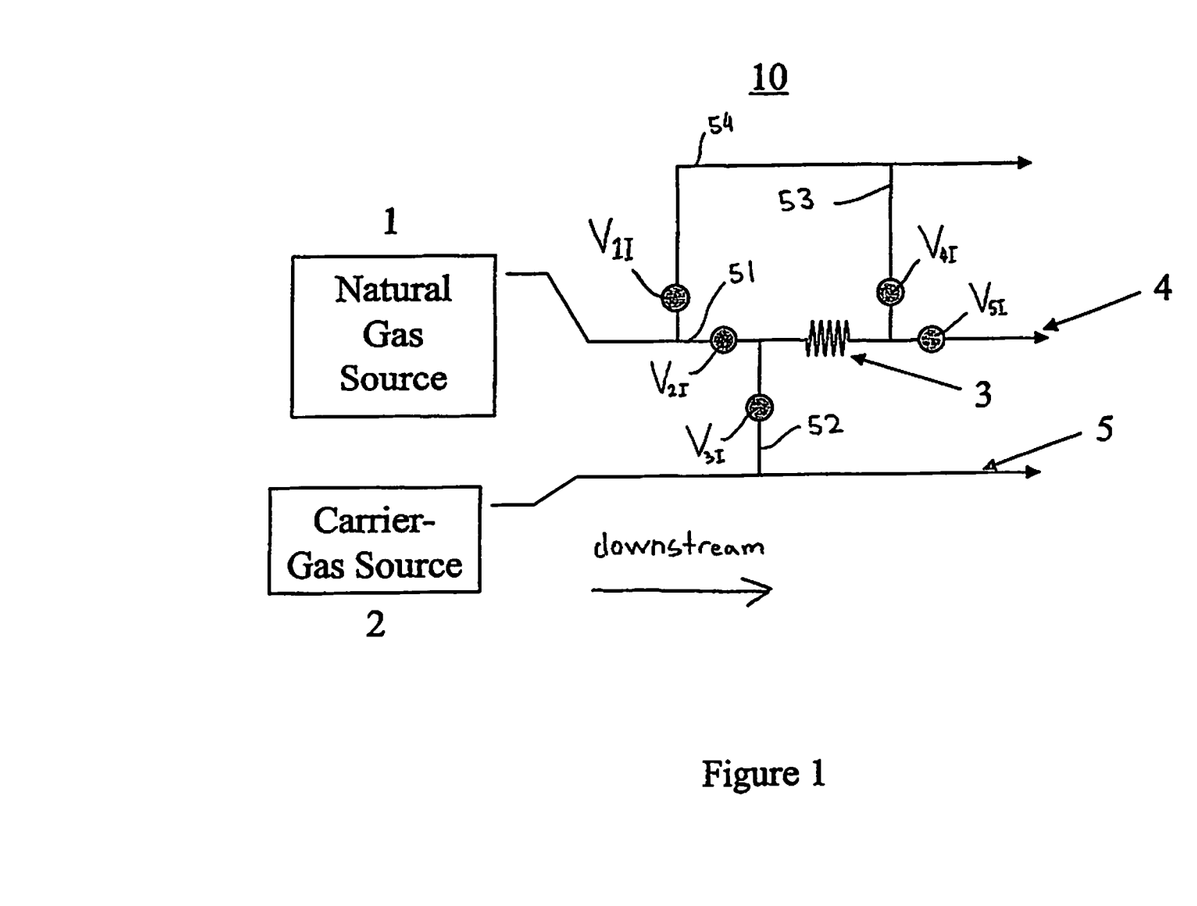
FIG. 1 shows a schematic view of an injector block in accordance with embodiments disclosed herein.

Referring to FIG. 1, a schematic view of an injector block 10 of a natural gas analyzer in accordance with embodiments disclosed herein is shown. The injector block 10 includes a sampling loop 3 that is connected to a natural gas source 1 and a carrier-gas source 2. Specifically, in this embodiment, the sampling loop 3 is connected to the natural gas source 1 through a sample inlet path 51, and connected to the carrier-gas source 2 through a carrier-gas path 52. The sample inlet path 51 and the carrier-gas path 52 may join each other upstream of the sampling loop 3, as shown, to supply the natural gas and carrier-gas to the sampling loop 3. Further, in this embodiment, a reference path 5 is directly connected to a carrier-gas source 2, in which the carrier-gas path 52 connects to the reference path 5 upstream of the sampling loop 3. The injector block 10 is used to take a gas sample from the natural gas source 1, and then inject the gas sample from the injector block 10 to column blocks connected downstream using carrier-gas from the carrier-gas source 2 (described more below). Further, for purposes of controlling the flow of the natural gas and carrier-gas within the injector block 10, the injector block 10 includes multiple valves $V_{1I}$ to $V_{5I}$ disposed on various paths, in which the valves $V_{1I}$ to $V_{5I}$ may be controlled between an open position and a closed position.

Generally, when not using the injector block 10, natural gas from the natural gas source 1 is diverted through a first branch 54. As such, a first valve $V_{1I}$ is open to allow flow through the first branch 54, and a second valve $V_{2I}$ is closed to block flow through the sample inlet path 51. A third valve $V_{3I}$ may also be closed to prevent carrier-gas from flowing into the sampling loop 3.

Then, when using the injector block 10, natural gas from the natural gas source 1 is diverted though the sampling loop 3 by opening the second valve $V_{2I}$ on the sample inlet path 51 and closing the first valve $V_{1I}$ on the first branch 54. To control the flow of the natural gas downstream of the sampling loop 3, a fourth valve $V_{4I}$ disposed on a vent path 53 is open, and a fifth valve $V_{5I}$ disposed on an analytical path 4 is closed. This allows the flow of the natural gas from the natural source 1 to join the first branch 54. Further, at this point, the third valve $V_{3I}$ is still closed to prevent carrier-gas from entering the sampling loop 3.

The sampling loop 3 is used to provide and retrieve a gas sample from the natural gas source 1 as the natural gas flows through the sampling loop 3. For example, in one embodiment, the sampling loop 3 may be a long capillary. In such an embodiment, the natural gas may flow to the long capillary for a controlled period of time, in which the size (e.g., volume) of the gas sample may be determined based upon the period of time of flow of the natural gas within the long capillary.

After a gas sample is retrieved with the sampling loop 3, the flow of the natural gas may be diverted away from the sampling loop 3 by closing the second valve $V_{2I}$ and opening the first valve $V_{1I}$. Further, the injector column 10 may then be used to inject the gas sample within the sampling loop 3 to column blocks located downstream (described more below). Specifically, to inject the gas sample, with the second valve $V_{2I}$ on the sample inlet path 51 remaining closed, the third valve $V_{3I}$ on the carrier-gas path is opened, the fourth valve $V_{4I}$ on the vent path 53 is closed, and the fifth valve $V_{5I}$ on the analytical path is opened. This enables carrier-gas from the carrier-gas source 2 to flow through the sampling loop 3 and carry the gas sample within the sampling loop 3 along the analytical path 4 to be separated amongst downstream column blocks.

Figure 2:
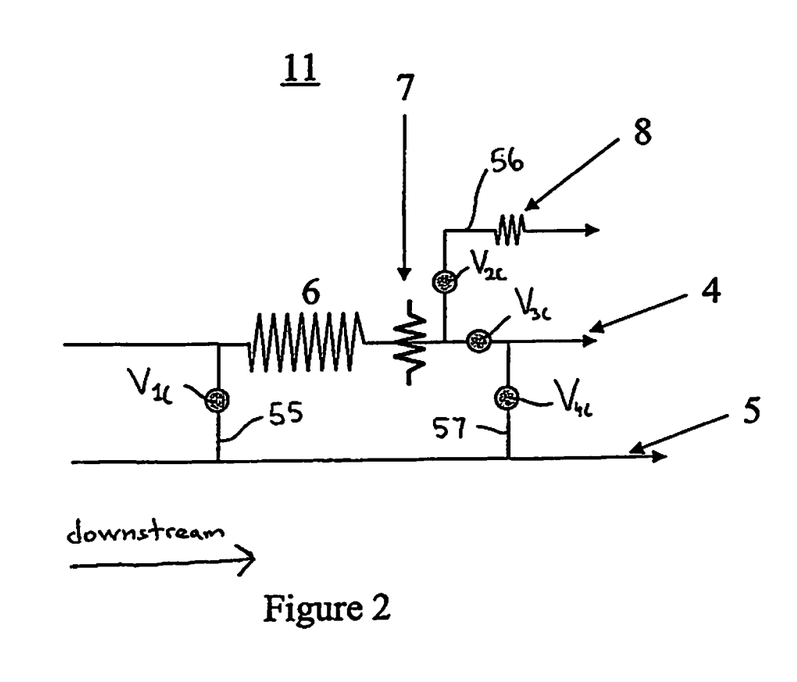
FIG. 2 shows a schematic view of a column block in accordance with embodiments disclosed herein.

Referring now to FIG. 2, a schematic view of a column block 11 of a natural gas analyzer in accordance with embodiments disclosed herein is shown. The column block 11, generally, is located downstream of the injector block 10 along the analytical path 4 and the reference path 5 to receive a gas sample carried by carrier-gas. The column block 11 includes a separation column 6 and a detector 7, both disposed along the analytical path 4. Further, the column block 11 includes a calibrated pressure drop 8 located downstream of the separation column 6 and the detector 7, and also includes multiple valves $V_{1C}$ to $V_{4C}$ disposed on various paths to control the flow of the gas sample and the carrier-gas within the column block 11.

As discussed above, the injector block 10 injects the gas sample with the carrier-gas into the column block 11 along the analytical path 4. When receiving this gas sample within the column block 11, only a third valve $V_{1C}$ located on the analytical path is open. The remaining valves, a first valve $V_{1C}$ on a first connection path 55, a fourth valve $V_{4C}$ on a second connection path 57, and a second valve $V_{2C}$ on a pressure drop path 56, all otherwise remain closed to allow the flow of the gas sample through the separation column 6.

As discussed above, the gas sample is received within the separation column 6 of the column block 11 by having carrier-gas from the carrier-gas source 2 carry along the gas sample. Using techniques developed and common within gas chromatography, the separation column 6, which includes a stationary phase disposed therein, then separates the gas sample into two or more different components, depending on the gas sample and the stationary phase (discussed more below). Specifically, the function of the stationary phase within the separation column is to separate the different components of the gas sample, thereby causing the different components to flow through the separation column at different rates and exit the separation column at different times. The separation of the components of the gas sample and the flow rate of the components of the gas sample is dependent upon the chemical and physical properties of the gas sample and the interaction of these components with the specific stationary phase used or disposed within the separation column.

As such, the unresolved components of the gas sample may be expelled from the separation column 6 first, followed by the resolved components of the gas sample. The detector 7 downstream of the column 6 along the analytical path 4 then detects the different components of the gas sample being expelled from the separation column 6. Generally, for gases with multiple components, such as natural gas, multiple column blocks 11 may be used to separate the gas sample into several smaller desired components. As such, some of the components passing through a first column block 11 may then be expelled to pass through a second column block 11, while the remaining components may then expelled from the gas analyzer altogether.

For example, in an embodiment having the gas sample separated into two different components, a resolved component and an unresolved component, the unresolved component may expel from the separation column 6 first. As the components of the gas sample exit the separation column 6 then, the detector 7 is used to detect the separate components, thereby differentiating between the unresolved component and the resolved component of the gas sample. Assuming that it is desired to separate the unresolved component further into multiple smaller components, this unresolved component of the gas sample may then be carried by carrier-gas further downstream along the analytical path 4 to another column block 11 with another separation column 6.

Accordingly, as the unresolved component of the gas sample is passed further downstream to be separated into more components, the resolved component of the gas sample may be eluted from the column block 11. As such, to elute the resolved component from the column block 11, the carrier-gas supplied from the injector block 10 may be stopped, such as by closing either one or both of the third and fifth valves $V_{3I}$ and $V_{5I}$ of the injector block 10 (shown in FIG. 1). Rather than supplying carrier-gas from the injector block 10, the first valve $V_{1C}$ of the column block 11 disposed on the first connection path 55 may be opened to supply carrier-gas from the reference path 5 to the separation column 6. At this time, the third valve $V_{3C}$ may be closed and a second valve $V_{2C}$ on a pressure drop path 56 may be opened to allow flow of carrier-gas through the separation column 6 and then along the pressure drop path 56. The carrier-gas passing through the separation column 6 will then elute the resolved component of the gas sample from the separation column 6 and exit the column block 11 through the pressure drop path 56. The calibrated pressure drop 8 located on the pressure drop path 56 may be used to control the pressure of the flow along the pressure drop path 56 such that the flow rate of the components of the gas sample and the carrier-gas may be consistent and comparable, independent of the flow path used. Further, after the unresolved component of the gas sample passes through the third valve $V_{3C}$ on the analytical path 4 and the third valve $V_{3C}$ is closed, the fourth valve $V_{4C}$ on the second connection path 57 may be opened such that carrier-gas from the reference path 5 may carry the unresolved component of the gas sample further downstream.

As mentioned above, depending on the composition of the gas being separated using gas chromatography, multiple column blocks may be used when separating the gas sample into different components. Natural gas, as described herein as any gas produced from oil or gas reservoirs from exploration to production, generally has many components, the main components being nitrogen, carbon dioxide, hydrogen sulfide, methane, in addition to various other alkanes. To separate out these various components of the natural gas from one another, several column blocks with various separation columns may be used within a series. Further, though oxygen is not naturally present within natural gas, oxygen may still get into the natural gas source and/or the gas sample. Therefore, oxygen may be another component of interest to be separated out from the gas sample. Because of the various components present within the gas sample, the preferable carrier-gas used within the embodiments disclosed herein may be helium. Helium already has a high mobility, in addition to not being a component of the natural gas within the gas sample, so this may help avoid complications when separating the components of the gas sample. However, those having ordinary skill in the art will appreciate that the present invention is not limited to only the use of Helium as the carrier-gas, and other gases such as nitrogen, argon, hydrogen, air, and other carrier-gases known in the art may be used.

Further, preferably capillary columns are used for the separation columns when separating the components of the gas sample. Capillary columns generally may have a very small diameter, such as about 100 micrometers ($3.94 \times 10^{-3}$ inches), and lengths ranging between 25-60 meters (82-197 feet). The inner walls of the capillary columns may then be coated with active materials to create the stationary phase within the column that separates the components of the gas sample when passing therethrough. These capillary columns are also generally flexible, so a very long capillary column may be wound into a small coil for use within the column block. Those having ordinary skill in the art, though, will appreciate that the present invention may not be limited to only the use of capillary columns, in which any separating column known in the art may be used within embodiments of the present invention.

Further still, preferably a thermal conductivity detector (TCD) is used for the detector to detect and differentiate between the separated components of the gas sample. Recent developments in technology have significantly decreased the sizes of TCDs, such as by micro-machining the TCDs, while still allowing for very accurate readings. Natural gas analyzers with these TCDs then may be very small, but capable of detecting traces of gases, such as down to a few parts-per-million (ppm). However, those having ordinary skill in the art will appreciate that the present invention is not so limited, and any detector known in the art, such as flame ionization detectors (FID), electron capture detectors (ECD), flame photometric detectors (FPD), photo-ionization detectors (PID), nitrogen phosphorus detectors, and hall electrolytic conductivity detectors, may be used without departing from the scope of the present invention. Each of these detectors may then include an electronic controller and signal amplifier when used within the natural gas analyzer.

Figure 3:
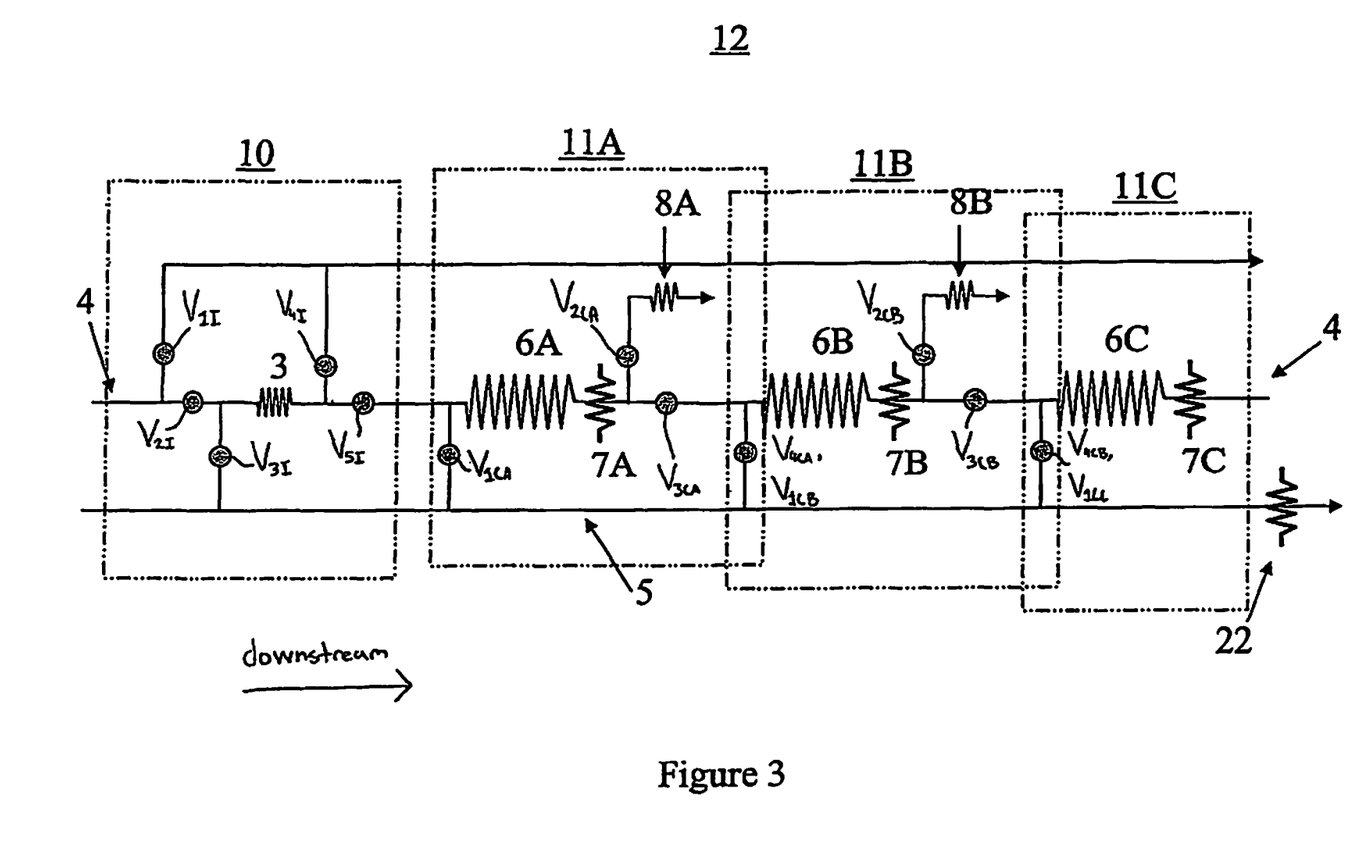
FIG. 3 shows a schematic view of a natural gas analyzer using gas chromatography in accordance with embodiments disclosed herein.

Referring now to FIG. 3, a schematic view of a natural gas analyzer 12 in accordance with embodiments disclosed herein is shown. In this embodiment, the natural gas analyzer 12 includes an injector block 10 and three column blocks 11A-11C. The three column blocks 11A-11C are connected in series downstream from the injector block 10. Specifically, a first column block 11A is connected to a second column block 11B, in which the first and second column blocks 11A and 11B share a valve $V_{4CA}$, $V_{1CB}$, and the second column block 11B is connected to a third column block 11C, in which the first and second column blocks 11A and 11B share a valve $V_{4CB}$, $V_{1CC}$. As discussed above, the injector block 10 includes a sampling loop 3, and each of the column blocks 11A-11C includes a separation column 6A-6C and a detector 7A-7C, respectively. Further, the first and second column blocks 11A and 11B may further include a calibrated pressure drop 8A and 8B, respectively, connected thereto.

As discussed above, the analytical path 4 is connected upstream to a natural gas source 1 (shown in FIG. 1), and the reference path 5 is connected upstream to a carrier-gas source 2 (also shown in FIG. 1). Disposed on the reference path 5 then may be a detector 22 for reference of the carrier-gas through reference path 5. Specifically, the information and data gathered from the detector 22 may be compared with the information and data gathered from the detectors 7A-7C for reference.

Using the natural gas analyzer 12, a gas sample of natural gas may then be taken from the natural gas source 1 and injected into the series of column blocks 11A-11C to be separated into components and quantified using gas chromatography. As such, to separate the gas sample into the main components of the natural gas, the columns 6A-6C of the column blocks 11A-11C, respectively, may each incorporate different stationary phases such that the columns 6A-6C may each be used to separate different components from the gas sample.

For example, in one embodiment, the first separation column 6A may include a low polarity stationary phase, such as squalane, dimethyl polysiloxane, or any other low polarity stationary phase known in the art, the second separation column 6B may include an adsorbing polymer stationary phase, such as a Porapak-Q or any other adsorbing polymer stationary phase known in the art, and the third column may include a molecular sieve stationary phase, such as a 5A molecular sieve type, a 13× molecular sieve type, or any other molecular sieve stationary phase known in the art. As such, each of the separation columns 6A-6C may be used to separate different components from the gas sample. Specifically, in such an embodiment, the first separation column 6A may be used to separate out butanes and any heavier components from the gas sample, in which an unresolved (i.e., unseparated) component of the gas sample may then be passed onto the second separation column 6B. Then, in the described embodiment, the second column 6B may be used to separate the carbon dioxide, ethane, hydrogen sulfide, water, and propane from the gas sample, in which a second unresolved component from the gas sample may then be passed onto the third separation column 6C. As such, in the described embodiment, the third column 6C may be used to separate the oxygen, nitrogen, and methane from the gas sample. During the use of this natural gas analyzer 12, the temperature may be controlled and maintained at a constant value to ensure reproducibility of the gas chromatography. For example, an oven may be used with the natural gas analyzer 12 to control temperatures from sub-ambient up to about 400° C. (752° F.).

Referring now to FIGS. 4-7, more schematic views of the natural gas analyzer 12 shown in FIG. 3 in accordance with embodiments disclosed herein are shown. In FIGS. 4-7, open valves are shown as void circles, and closed valves are shown as plain circles. Specifically, FIGS. 4-7 show the process of taking a gas sample from the natural gas source 1 (not shown) and passing the gas sample through the natural gas analyzer 12 to separate the components within the gas sample using gas chromatography. Further, in these embodiments, the separation column 6A of the first column block 11A includes a low polarity stationary phase, the separation column 6B of the second column block 11B includes an adsorbing polymer stationary phase, and the separation column 6C of the third column block 11C includes a molecular sieve stationary phase. However, those having ordinary skill in the art will appreciate that the embodiments of the present invention are not so limited, and the separation columns may include any stationary phase known in the art.

Figure 4:
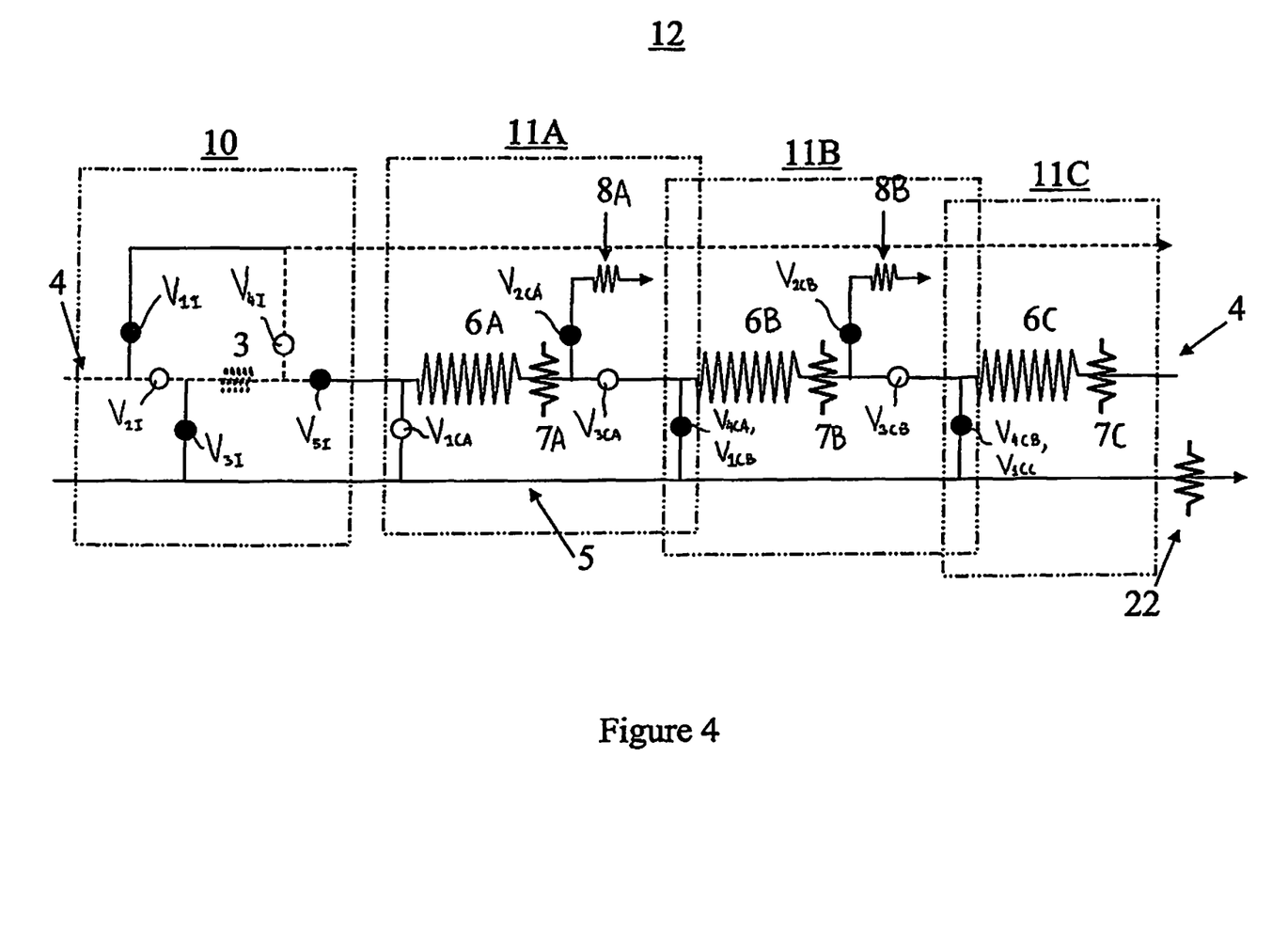
FIGS. 4-7 show schematic views of the natural gas analyzer shown in FIG. 3 during use in accordance with embodiments disclosed herein.

First, as shown in FIG. 4, the second and fourth valves $V_{2I}$ and $V_{4I}$ of the injector block 10 are opened, while the first, third, and fifth valves $V_{1I}$, $V_{3I}$, and $V_{5I}$ of the injector block 10 are closed. This allows natural gas to pass from the natural gas source 1 along the analytical path 4 and through the sampling loop 3. As described above, the natural gas is passed through the sampling loop 3 for a controlled amount of time to receive a gas sample having a controlled size or amount.

Figure 5:
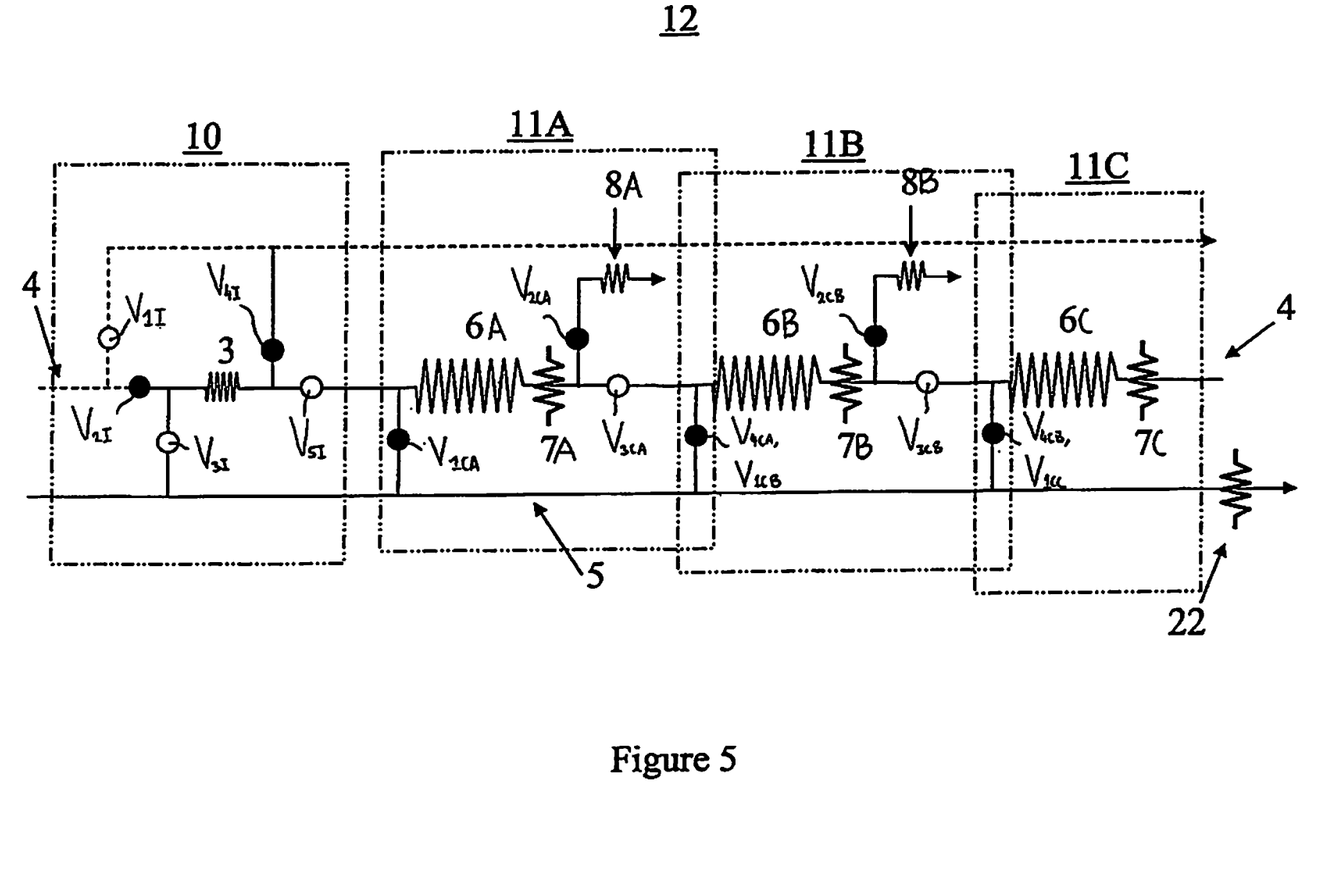

Second, as shown in FIG. 5, after a gas sample is taken from the natural gas source 1, the first valve $V_{1I}$ of the injector block 10 may be opened, and the second valve $V_{2I}$ of the injector block 10 may be closed so as to divert any more natural gas from entering the sampling loop 3. As such, this gas sample may be passed from the injector block 10 to the column blocks 11A-11C by opening the third and fifth valves $V_{3I}$ and $V_{5I}$ of the injector block 10 and closing the fourth valve $V_{4I}$ of the injector block 10. This may allow carrier-gas from the carrier-gas source 2 (not shown) to enter the sampling loop 3 from the reference path 5 and carry the gas sample from the injector block 10 to the first column block 11A along the analytical path 4. Also, to allow the gas sample to flow along the analytical path 4, the third valves $V_{3CA}$ and $V_{3CB}$ of the first and second column blocks 11A and 11B, respectively, are open, while remaining valves (the first, second, and fourth valves $V_{1CA}$, $V_{2CA}$, $V_{4CA}$, $V_{1CB}$, $V_{2CB}$, $V_{4CB}$, and $V_{1CC}$ of the first, second, and third column blocks 11A, 11B, and 11C) are closed.

Further, still referring to FIG. 5, as the gas sample passes through the separation column 6A of the first column block 11A having the low polarity stationary phase, the gas sample may have the butanes and any heavier components separated from an unresolved component of the gas sample. As such, the unresolved component of the gas sample may exit the separation column 6A first, followed by the butanes and heavier components of the gas sample. The detector 7A may be used to detect the components of the gas sample exiting the separation column 6A, in which the detector 7A will allow the unresolved component of the gas sample to continue along the analytical path 4. After the unresolved component of the gas sample finishes exiting from the separation column 6A, the detector 7A will detect that the unresolved component of the gas sample has passed and thereby begin the process of eluting the butane and heavier components of the gas sample from the natural gas analyzer 12.

Figure 6:
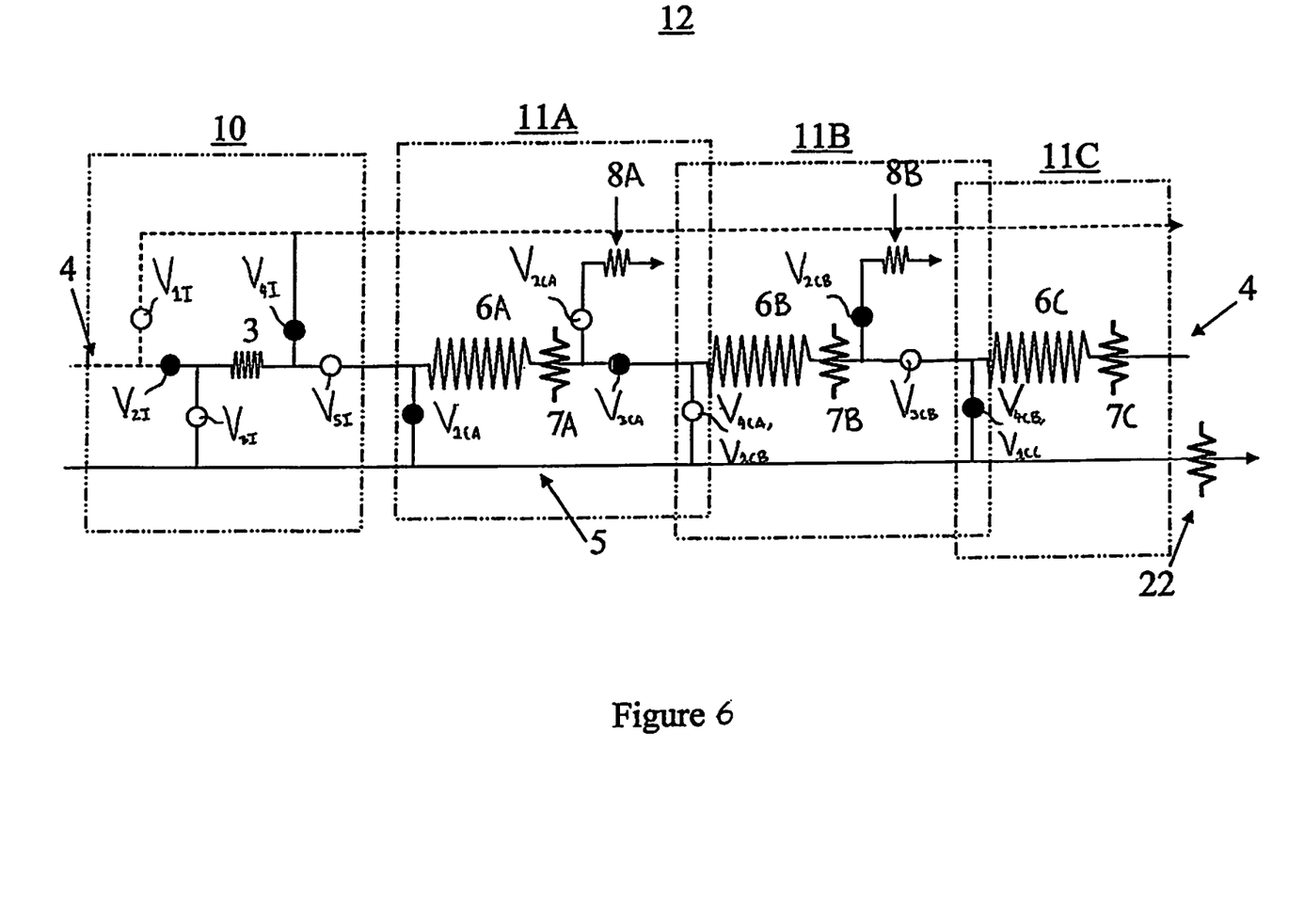

Next, as shown in FIG. 6, to elute the butane and heavier components from the natural gas analyzer 12, the second valve $V_{2CA}$ of the first column block 11A is opened, and the third valve $V_{3CA}$ of the first column block 11A is closed. This allows the butanes and the heavier components of the gas sample, which exit the separation column 6A slower than the unresolved component of gas sample, to pass through the calibrated pressure drop 8A of the first column block 11A and exit the natural gas analyzer 12. When eluting the butanes and heavier components from the separation column 6A, carrier-gas may be supplied by opening either one of the third valve $V_{3I}$ of the injector block 10 and the first valve $V_{1CA}$ of the first column block 11A and closing the other.

Further, to pass the unresolved component of the gas sample through the separation column 6B of the second column block 11B, the first valve $V_{1CB}$ of the second column block 11B (also the fourth valve $V_{4CA}$ of the first column block 11A) may be opened to allow carrier-gas from the reference path 5 to pass through the separation column 6B along the analytical path 4. As the unresolved component of the gas sample passes through the separation column 6B of the second column block 11B having the adsorbing polymer stationary phase, the unresolved gas sample component may have the carbon dioxide, ethane, hydrogen sulfide, water, and propane separated from a second unresolved component of the gas sample. As such, the second unresolved component of the gas sample may exit the separation column 6B first, followed by the separated components of the gas sample (the carbon dioxide, ethane, hydrogen sulfide, water, and propane). The detector 7B may be used to detect the components of the gas sample exiting the separation column 6B, in which the detector 7B will allow the second unresolved component of the gas sample to continue along the analytical path 4. After the second unresolved component of the gas sample finishes exiting from the separation column 6B, the detector 7B will detect that the second unresolved component of the gas sample has passed and thereby begin the process of eluting the separated components of the gas sample from the natural gas analyzer 12.

Figure 7:
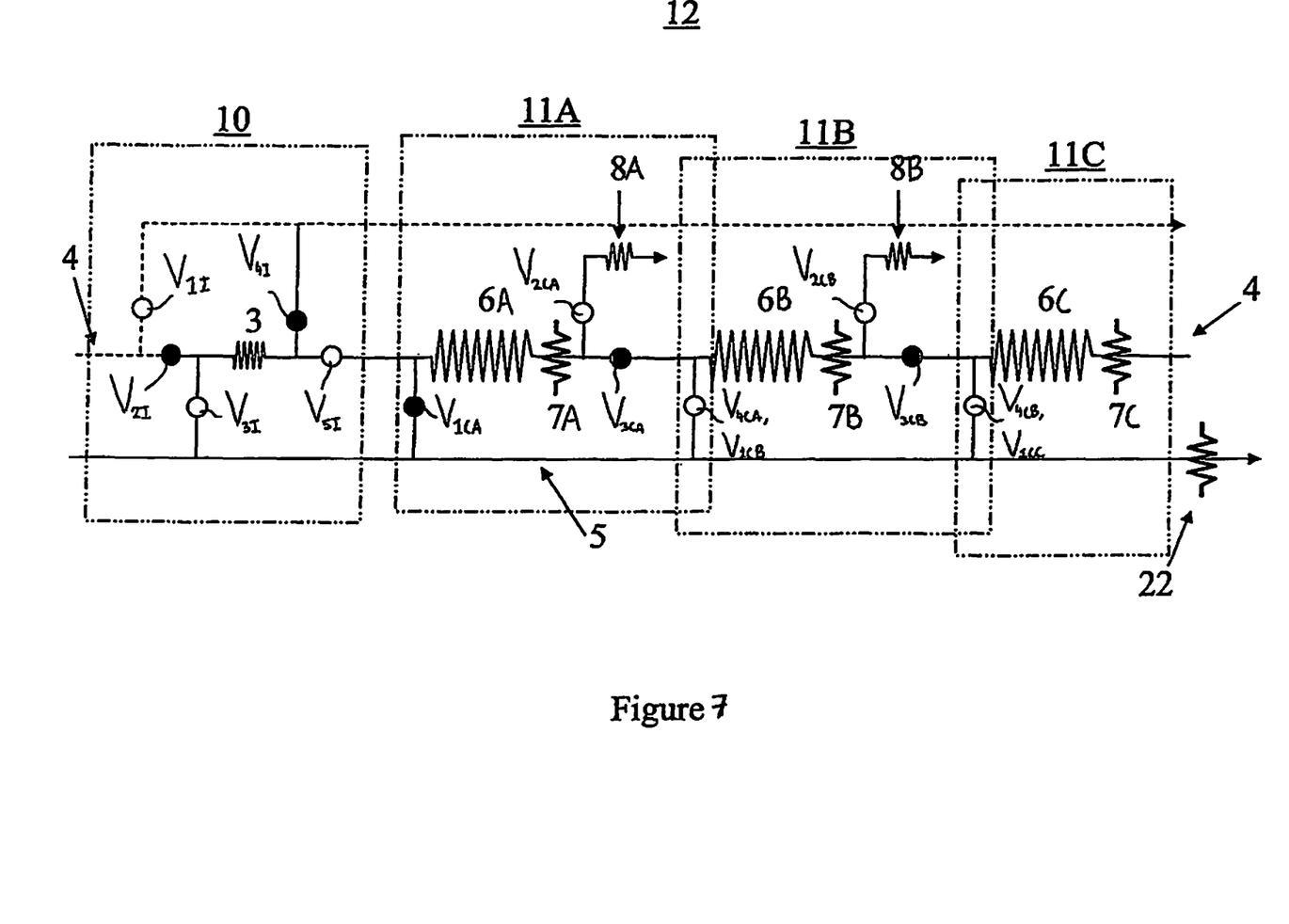

Finally, as shown in FIG. 7, to elute the separated components of the gas sample (the carbon dioxide, ethane, hydrogen sulfide, water, and propane) from the natural gas analyzer 12, the second valve $V_{2CB}$ of the second column block 11B is opened, and the third valve $V_{3CB}$ of the second column block 11B is closed. This allows the separated components of the gas sample, which may exit the separation column 6B slower than the second unresolved component of gas sample, to pass through the calibrated pressure drop 8B of the second column block 11B and exit the natural gas analyzer 12. When eluting the separated components from the separation column 6B, carrier-gas may be supplied by opening the first valve $V_{1CB}$ of the second column block 11B (also the fourth valve $V_{4CA}$ of the first column block 11A). During this time, carrier-gas may continue to pass through the separation column 6A of the first column block 11A to continue to elute the butane and heavier components from the separation column 6A.

Further, to pass the second unresolved component of the gas sample through the separation column 6C of the third column block 11B, the first valve $V_{1CC}$ of the third column block 11C (also the fourth valve $V_{4CB}$ of the second column block 11B) may be opened to allow carrier-gas from the reference path 5 to pass through the separation column 6C along the analytical path 4. As the second unresolved component of the gas sample passes through the separation column 6B of the second column block 11B having the molecular sieve stationary phase, the second unresolved gas sample component may have the oxygen, nitrogen, and methane separated within the gas sample. As such, the oxygen, nitrogen, and methane may exit the separation column 6C at different times, in which the detector 7C may be used to detect the components of the gas sample exiting the separation column 6C. In this embodiment, then, the separated components may continue down the analytical path 4 to be eluted from the natural gas analyzer 12.

Using this natural gas analyzer 12, as shown in FIGS. 4-7 in the example embodiment, the relative concentration of the components of the natural gas source, including non-hydrocarbons such as nitrogen, carbon dioxide, hydrogen sulfide, and water, may each be determined. Further, oxygen may be detected within the natural gas analyzer 12 to quantify and calculate the air content within the gas sample and natural gas source, thereby also determining the nitrogen content of the natural gas source. Further, using this natural gas analyzer 12 allows the same gas sample to be used for the entire natural gas analysis. In the typical laboratory methods, a different sample is injected into each separation column. However, in accordance with embodiments disclosed herein, the same gas sample may be used by multiple separation columns, thereby ensuring coherence between the separation columns and reducing factors of error. Furthermore, by using this natural gas analyzer 12, this may prevent column pollution by having components of the gas sample permanently trapped within the separation columns. If components of the gas sample become trapped within the separation columns, the separation columns may become damaged and compromise the reliability of the natural gas analyzer. However, in accordance with embodiments disclosed herein, the components of the natural gas analyzer may be entirely eluted from the natural gas analyzer because of the individual control of the separation columns within column blocks.

Further, in accordance with embodiments disclosed herein, to improve the versatility of the natural gas analyzer, the natural gas analyzer may be machined (e.g., micro-machined) or formed onto a micro-chip. For example, the schematic of the natural gas analyzer 12 shown in FIG. 3 may be machined onto a micro-chip, such as a silicon micro-chip, such that the natural gas analyzer includes a gas chromatograph as a micro-electro-mechanical system (MEMS). As such, the sampling loop, each of the separation columns, and each of the valves of the natural gas analyzer may be formed onto the micro-chip. Further, due to the properties of natural gas and the components included therein, preferably the micro-chip of the natural gas analyzer is formed from a material that is resistant to sour gases. For example, the micro-chip of the natural gas analyzer may be formed from silicon, which is chemically inert to the sour gas components of natural gas, such as carbon dioxide and hydrogen sulfide.

Figure 8:
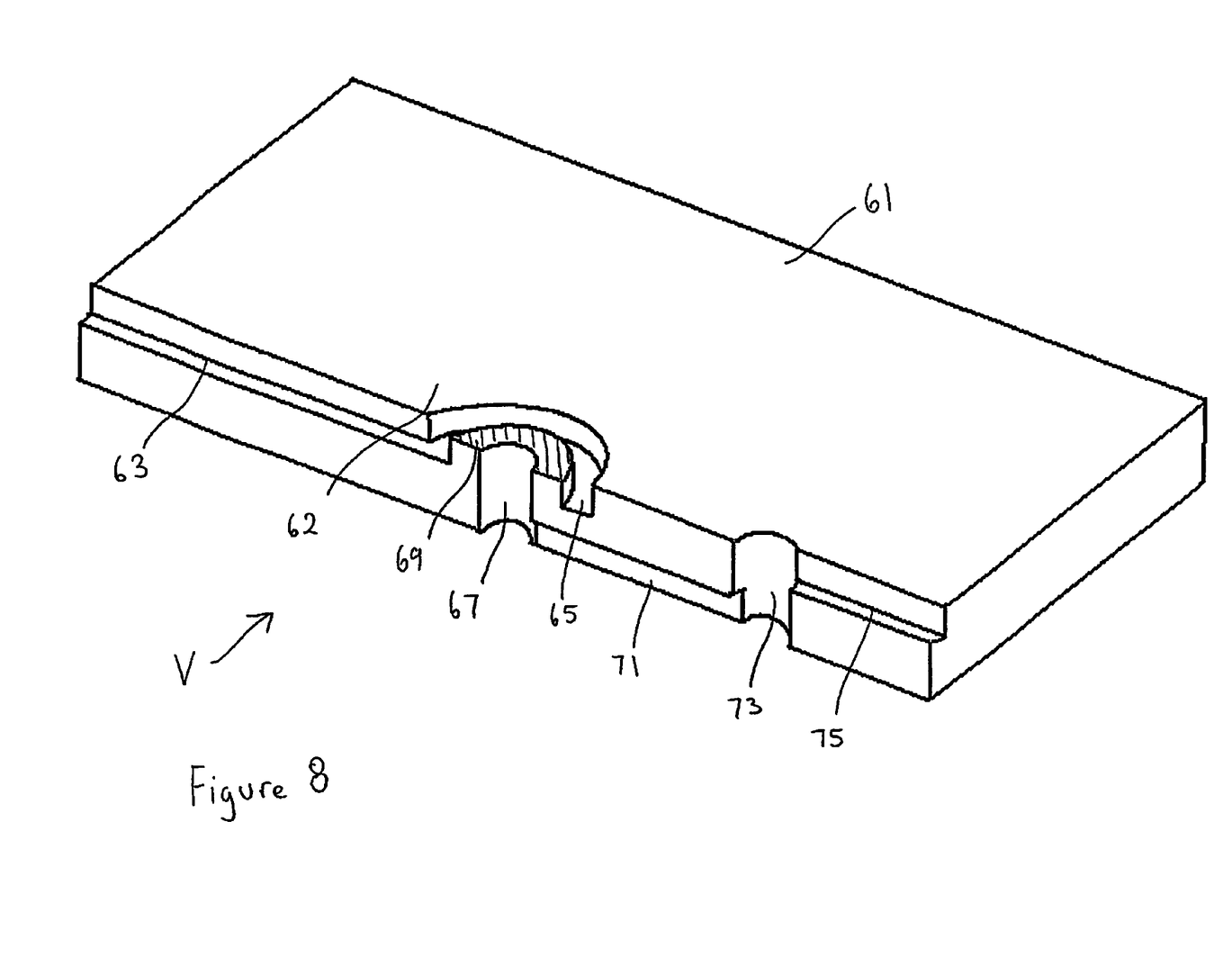
FIG. 8 shows a perspective view of a cross-section of a micro-chip of a valve in accordance with embodiments disclosed herein.
Figure 9A:
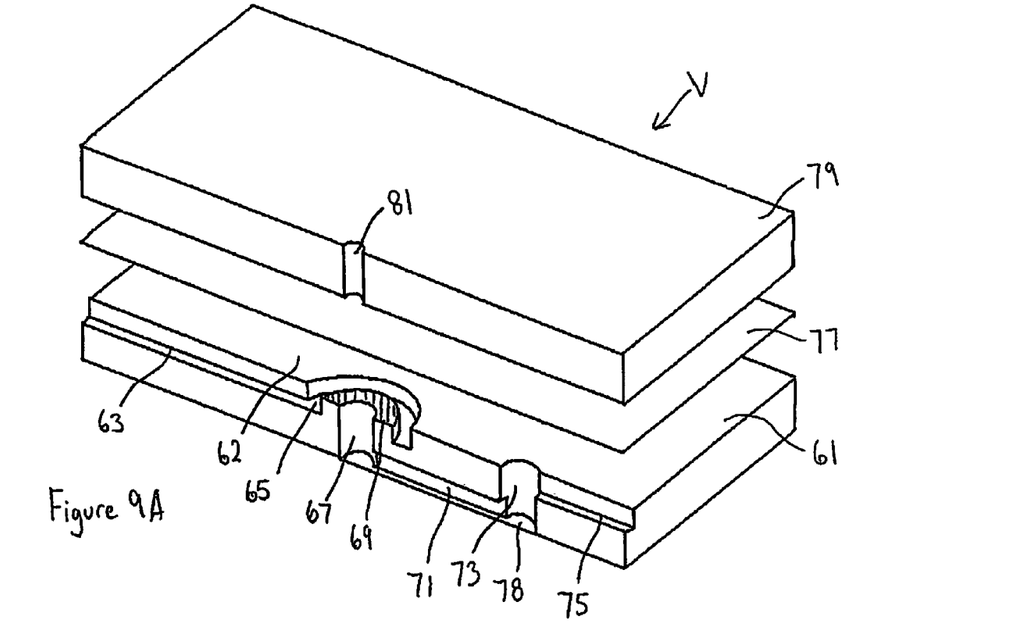
FIGS. 9A and 9B show an exploded view and a perspective view of a cross-section of a valve in accordance with embodiments disclosed herein.
Figure 9B:
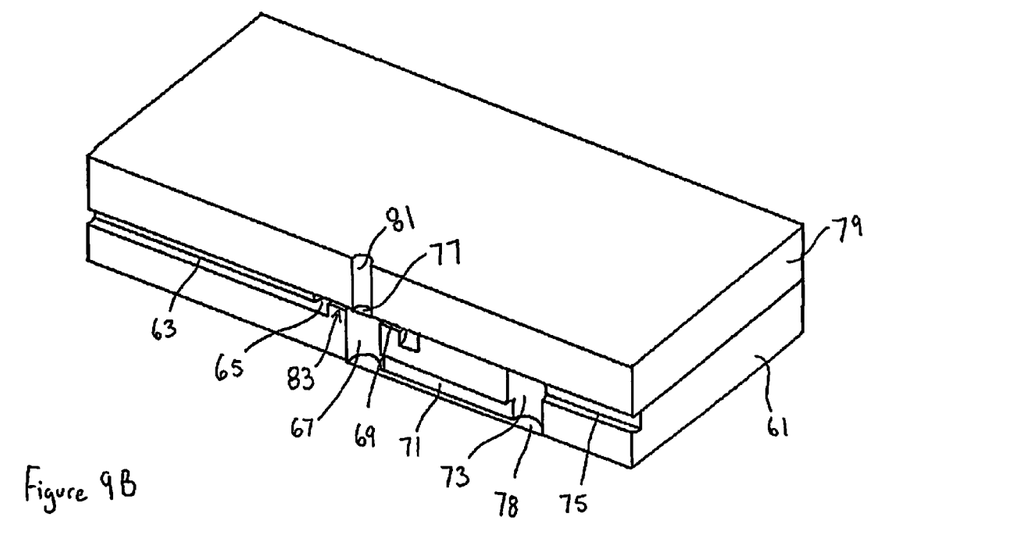

Referring now to FIGS. 8, 9A, and 9B, perspective views of a cross-section of a valve V in accordance with embodiments disclosed herein is shown. Specifically, as shown in FIG. 8, the valve V includes multiple paths and conduits machined or formed onto a micro-chip 61. In this embodiment, the valve V includes a first path 63 that receives gas (e.g., natural gas), in which the valve may selectively be opened and closed to allow the gas to pass therethrough. As shown, the first path 63 connects to a loop groove 65, and the loop groove 65 then connects to a first conduit 67. Preferably, as shown, the loop groove 65 surrounds the first conduit 67, in which the loop groove 65 may be formed from any closed shape known in the art. Further, when forming the valve V, a top surface 69 of the first conduit 67 protrudes slightly below a top surface 62 of the micro-chip 61. The first conduit 67 then connects to a second conduit 73 via a second path 71, and a third path 75 connects to the second conduit 73.

Referring now to FIGS. 9A and 9B, an exploded view and a perspective view, respectively, of a cross-section of the valve V in accordance with embodiments disclosed herein is shown. Specifically, in addition to the micro-chip 61, the valve V may further include a first flexible membrane 77, a second flexible membrane 78, and a rigid substrate 79. As shown, the first flexible membrane 77 is disposed on the top surface 69 of the micro-chip 61, the second flexible membrane 78 is disposed on the bottom of the micro-chip 61, and the rigid substrate 79 is disposed on top of the flexible membrane 77. The rigid substrate 79 then includes a port 81 formed therein such that when the rigid substrate 79 is disposed on top of the first flexible membrane 77 and the micro-chip 61, the port 81 of the rigid substrate 79 is in alignment with the first conduit 67 of the micro-chip 61.

Because the top surface 69 of the first conduit 67 protrudes slightly below the top surface 62 of the micro-chip 61, a small gap 83 is formed between the top surface 69 of the first conduit 67 and the first flexible membrane 77 when the valve V is assembled (as shown in FIG. 9B). As such, the valve V is open when the small gap 83 is present because gas may pass all the way from the first path 63, through the loop groove 65 and first conduit 67, to the third path 75, thereby allowing flow of gas through the valve V. However, to instead close the valve V, pressure may be introduced to the valve V through the port 81. When pressure is introduced through the port 81, the pressure will push the first flexible membrane 77 down upon the top surface 69 of the first conduit 67, thereby closing the small gap 83. When the small gap 83 is closed, the valve V is closed to not allow gas to pass through because no gap is present between the loop groove 65 and the first conduit 67. As such, the natural gas analyzer may use this technology for the valves of the present disclosure, in which carrier-gas may be used to supply pressure to any of the ports for opening and closing the valves.

Similar to the micro-chip, preferably the flexible membranes and the rigid substrate are formed from materials inert to the sour gas components of natural gas. For example, the flexible membranes may be formed from polymer film, such as PEEK polymer film available from Victrex®, or any other flexible membrane known in the art, and the rigid substrate may be formed from glass, or any other rigid substrate known in the art.

Preferably, to improve the adaptability and versatility of the natural gas analyzer in accordance with embodiments disclosed herein, the natural gas analyzer may either be enclosed within an explosion proof housing, or the natural gas analyzer may use intrinsically safe electrical components. Because the size of the natural gas analyzer may be very small and compact, the electronic controls and signal processing will have low energy consumptions. As such, these low energy consumptions should facilitate having an intrinsically safe design for the natural gas analyzer.

Embodiments of the present invention may include one or more of the following advantages. First, because of the relative size of the micro-chip, a natural gas analyzer in accordance with embodiments disclosed herein may be very versatile for all types of environments. Next, a natural gas analyzer in accordance with embodiments disclosed herein may also be used in other industries. Specifically, rather than being limited to natural gas, the natural gas analyzer may be incorporated into virtually any application that utilizes gas chromatography. Further, a natural gas analyzer in accordance with embodiments disclosed herein may provide economic advantages. Specifically, because of the size and simplicity of the natural gas analyzers, the production costs may be improved by using components and materials commonly available. Finally, a natural gas analyzer in accordance with embodiments disclosed herein may also extend the types of analyses for gas chromatography that are performed because of the rigidity and resistance of the analyzer. Specifically, the natural gas analyzer formed on the micro-chip may begin to be incorporated into extreme conditions, such as bottom hole conditions within a wellbore.

The miniaturized gas analyzer of the present invention overcomes the limitations of the prior art by offering built-in flexibility for analyzing different types of natural gas. The overall dimensions of the analyzer offer an advance over the prior art and are preferably from about 1-20 cm, more preferably 1-15 cm and even more preferably from about 1-10 cm.

While the invention has been described with respect to a limited number of embodiments, those skilled in the art, having benefit of this disclosure, will appreciate that other embodiments may be devised which do not depart from the scope of the invention as disclosed herein. Accordingly, the scope of the invention should be limited only by the attached claims.

The invention claimed is:

1. A miniaturized gas analyzer formed onto a single micro-chip, wherein the gas analyzer comprises:
    an injector block comprising:
        a sample inlet path connected to a natural gas inlet source to receive composite gas;
        a reference path connected to a carrier-gas inlet source to receive carrier-gas, wherein the reference path includes a reference detector for reference of the carrier-gas;
        a carrier-gas path connecting the sample inlet path to the reference path;
        a sampling loop having an input and an output, wherein the input of the sampling loop is connected to the sample inlet path and the carrier-gas path; wherein the output expels the received composite gas carried by the carrier-gas as a gas sample; and
    a first column block and a second column block, wherein the first and second column blocks each comprise:
        a separation column having an input to receive the gas sample and for separating the gas sample into components; and
        a detector arranged to receive the components of the gas sample from an output of the separation column and to differentiate the components into resolved components and unresolved components;
    wherein the injector block and the first and second column blocks are arranged in series on an analytical path of the micro-chip such that the gas sample expelled by the output of the sampling loop is received within the first column block,
    wherein the output of the sampling loop is connected to the analytical path and a vent path,
    wherein a first branch path diverges from the sample inlet path and connects to the vent path to bypass the sampling loop,
    wherein the unresolved component is expelled by the first column block and received within the second column block.

2. The miniaturized gas analyzer according to claim 1, further comprising a third column block arranged in series on the analytical path such that a second unresolved component of the gas sample expelled by the second column block is received within the third column block.

3. The miniaturized gas analyzer according to claim 1, wherein the separation column of the first column block comprises a low polarity stationary phase, the separation column of the second column block comprises an adsorbing polymer stationary phase, and the separation column of the third column block comprises a molecular sieve stationary phase.

4. The miniaturized gas analyzer according to claim 1, wherein the injector block further comprises five valves, a first valve to a fifth valve, wherein each valve has an open position and a closed position;
    wherein the first valve is disposed on the first branch path;
    wherein the second valve is disposed on the sample inlet path;
    wherein the third valve is disposed on the carrier-gas path;
    wherein the fourth valve is disposed on the vent path; and
    wherein the fifth valve is disposed on the analytical path.

5. The miniaturized gas analyzer according to claim 4, wherein at least one of the valves of the injector block and the first column block is formed onto the micro-chip and comprises:

a flexible membrane disposed adjacent to the micro-chip; and a rigid substrate disposed adjacent to the flexible membrane.

6. The miniaturized gas analyzer according to claim 5,
wherein the valve comprises a loop groove and a conduit formed onto the micro-chip;
wherein the loop groove surrounds the conduit;
wherein a top surface of the conduit protrudes slightly below a top surface of the micro-chip;
wherein the rigid substrate comprises a port formed therein; and
wherein the micro-chip and the rigid substrate are arranged such that the conduit and the port are in alignment.

7. The miniaturized gas analyzer according to claim 1,
wherein the input of the separation column of the first column block is connected to the analytical path, wherein the analytical path is connected to the reference path upstream of the input of the separation column through a first connection path;
wherein the output of the separation column of the first column block is connected to the analytical path and connected to a calibrated pressure drop through a pressure-drop path, wherein the pressure drop path diverges from the analytical path, wherein the analytical path is connected to the reference path downstream of the output of the separation column through a second connection path; and
wherein the detector is located on the analytical path between the output of the separation column and the pressure drop path.

8. The miniaturized gas analyzer according to claim 7, wherein the first column block further comprises four valves, a first valve to a fourth valve, wherein each valve has an open position and a closed position;
wherein the first valve is disposed on the first connection path;
wherein the second valve is disposed on the pressure-drop path;
wherein the third valve is disposed on the analytical path; and
wherein the fourth valve is disposed on the second connection path.

9. The miniaturized gas analyzer according to claim 1, further comprising a calibrated pressure drop connected downstream to the output of at least one of the first and second column blocks.

10. The miniaturized gas analyzer according to claim 1, wherein temperature for the injector block and all of the column blocks is at a constant value.

11. A method of analyzing natural gas using a miniaturized gas analyzer formed onto a micro-chip, the method comprising:
sampling a volume of natural gas with a sampling loop of an injector block of the miniaturized gas analyzer to create a gas sample;
injecting the gas sample from the injector block to a first column block of the miniaturized gas analyzer using carrier-gas from a reference path of the miniaturized gas analyzer;
separating the gas sample into an unresolved component and a resolved component using a separation column of the first column block;
sending the unresolved component of the gas sample from the first column block to a second column block; and
venting the resolved component of the gas sample from first column block using carrier-gas from the reference path.

12. The method of analyzing natural gas according to claim 11, further comprising:
separating the unresolved component of the gas sample into a second unresolved component and a second resolved component using a separation column of the second column block;
sending the second unresolved component of the gas sample from the second column block to a third column block; and
venting the second resolved component of the gas sample from second column block using carrier-gas from the reference path.

13. The method of analyzing natural gas according to claim 12, wherein the separation column of the first column block is used to separate butanes and heavier components from the gas sample, the separation column of the second column block is used to separate carbon dioxide, ethane, hydrogen sulfide, water, and propane from the gas sample, and a separation column of the third column block is used to separate oxygen, nitrogen, and methane from the gas sample.

14. The method of analyzing natural gas according to claim 11, wherein the first column block comprises a detector to switch the first column block from sending the unresolved component of the gas sample to venting the resolved component of the gas sample.

* * * * *